United States Patent
Thomson et al.

(10) Patent No.: US 9,633,433 B1
(45) Date of Patent: Apr. 25, 2017

(54) SCANNING SYSTEM AND DISPLAY FOR ALIGNING 3D IMAGES WITH EACH OTHER AND/OR FOR DETECTING AND QUANTIFYING SIMILARITIES OR DIFFERENCES BETWEEN SCANNED IMAGES

(71) Applicant: Intellimed Systems, LLC, Cincinnati, OH (US)

(72) Inventors: Paul E. Thomson, Cincinnati, OH (US); Adam G. Gerlach, New Bremen, OH (US); Mark F. Smith, Amelia, OH (US)

(*) Notice: Subject to any disclaimer, the term of this patent is extended or adjusted under 35 U.S.C. 154(b) by 42 days.

(21) Appl. No.: 14/453,908

(22) Filed: Aug. 7, 2014

Related U.S. Application Data

(60) Provisional application No. 61/863,580, filed on Aug. 8, 2013.

(51) Int. Cl.
  *G06K 9/00* (2006.01)
  *G06T 7/00* (2017.01)
  *G06K 9/62* (2006.01)

(52) U.S. Cl.
  CPC .......... *G06T 7/0016* (2013.01); *G06K 9/6201* (2013.01)

(58) Field of Classification Search
  CPC .................. G06T 7/0016; G06K 9/6201
  See application file for complete search history.

(56) References Cited

U.S. PATENT DOCUMENTS

| | | | |
|---|---|---|---|
| 4,275,741 A | 6/1981 | Edrich | |
| 4,445,516 A | 5/1984 | Wollnik et al. | |
| 4,530,367 A | 7/1985 | Desjardins et al. | |
| 5,311,109 A | 5/1994 | Ozawa | |
| 5,325,449 A | 6/1994 | Burt et al. | |
| 5,941,833 A | 8/1999 | Lipman | |

(Continued)

OTHER PUBLICATIONS

Del Bimbo et al., "Retrieval by Content Similarity of 3D Models Using Spin Images" Annales Des Telecommunications, Dec. 2005, vol. 60, Issue 11-12, pp. 1360-1378.

(Continued)

*Primary Examiner* — Nirav G Patel
(74) *Attorney, Agent, or Firm* — Mark F. Smith; Smith Brandenburg Ltd

(57) ABSTRACT

The subject invention is a scanning system and display and more particularly a scanning system and display for detecting and quantifying similarities or differences between stored data and data collected from a scan. The system operates to perform surface scans and/or deep scans or a combination thereof and utilizes a method or process that decreases the time required for calculating a pose estimate thus increasing its performance thereby making it more practical for many applications that require real-time operations. In a preferred embodiment of the invention the system comprises one or more sensing components for scanning and measuring various surface or internal features of an object and determines differences between data obtained from two or more scans. Preferably the system can operate to scan numerous objects including mechanical objects, biological objects or medical conditions, artifacts, geographical objects, agricultural objects, or used in conjunction with robotic manufacturing systems, robotic surgical systems, aircraft systems, and marine applications.

16 Claims, 8 Drawing Sheets

(56) References Cited

U.S. PATENT DOCUMENTS

| | | | |
|---|---|---|---|
| 6,057,925 | A | 5/2000 | Anthon |
| 7,226,426 | B2 | 6/2007 | Thomson |
| 7,734,077 | B2 | 6/2010 | Hirsch et al. |
| 7,957,583 | B2 | 6/2011 | Boca et al. |
| 7,968,845 | B1 | 6/2011 | Wagner |
| 8,035,637 | B2 | 10/2011 | Kriveshko |
| 2002/0087274 | A1 | 7/2002 | Alexander et al. |
| 2002/0093115 | A1* | 7/2002 | Jang ............... B29C 67/0081 264/113 |
| 2003/0091226 | A1 | 5/2003 | Cahill et al. |
| 2004/0019269 | A1 | 1/2004 | Schaefer et al. |
| 2005/0041843 | A1 | 2/2005 | Sawyer |
| 2005/0288589 | A1 | 12/2005 | Houle et al. |
| 2008/0253612 | A1 | 10/2008 | Reyier et al. |
| 2008/0262869 | A1 | 10/2008 | Bronn |
| 2008/0285831 | A1* | 11/2008 | Kirchberg ............. G06T 19/00 382/131 |
| 2009/0279672 | A1 | 11/2009 | Reiner |
| 2011/0082667 | A1* | 4/2011 | Ibarz .................... G06T 15/503 703/1 |

OTHER PUBLICATIONS

Huber, Automatic 3D Modelling Using Range Images Obtained from Unknown Viewpoints: IEEE Proceedings, Third International Conference on 3D Digital Imaging and Modeling, 2001, pp. 153-160.

Jurgen Assfalg et al., Content-Based Retrieval of 3D Objects Using Spin Image Signatures, Apr. 2007, pp. 589-599, vol. 9, No. 3, IEEE Transactions on Multimedia.

H, Quynh Dinh et al., "Multi-Resolution Spin-Images" 2006, Proceedings of the 2006 IEEE Vomputer Society Conference on Computer Vision and Pattern Recognition.

Berthold K. Horn, "Closed-Form Solution of Absolute Orientation Using Unit Quaternions" vol. 4, pp. 629- ,Apr. 1987, Optical Society of America.

Andrew Edie Johnson, "Spin-Images; A Representation for 3D Surface Matching" Aug. 13, 1997, Carnegie Mellon University.

* cited by examiner

SCANNING SYSTEM AND DISPLAY FOR ALIGNING 3D IMAGES WITH EACH OTHER AND/OR FOR DETECTING AND QUANTIFYING SIMILARITIES OR DIFFERENCES BETWEEN SCANNED IMAGES

CROSS-REFERENCE TO RELATED APPLICATION

The present invention relates to and claims benefit to U.S. Provisional Patent Application Ser. No. 61/863,580, filed Aug. 8, 2013 entitled Scanning System and Display, which is incorporated herein in its entirety herein.

COPYRIGHT NOTIFICATION

Portions of this patent application contain materials that are subject to copyright protection. The copyright owner has no objection to the facsimile reproduction by anyone of the patent document or the patent disclosure, as it appears in the Patent and Trademark Office patent file or records. The copyright owner, however, otherwise reserves all copyright rights whatsoever.

BACKGROUND OF THE INVENTION

The subject invention is a scanning system and display and more particularly a scanning system and display for detecting and quantifying similarities or differences between stored data (or images) and data collected from scans or from other scans.

There are many disparate fields in which human senses are used as measuring tools. These fields are often specialized, technical, or industrial, and yet workers in these areas still acquire and gauge data using one or more of their biological senses. Clearly, given the technical nature and great importance of many of these fields, a need exists for a system that can rapidly, accurately, precisely, and objectively acquire and measure scanned data and automatically compare these data to a standard, should such a standard exist or to one or more previous scans.

Systems have been developed for use in assessing medical conditions using various imaging systems, such a surface scanning systems, as well as systems using X-rays, gamma rays, radio-frequency waves, electron-position annihilation, electron, ions and magnetic particles (hereinafter referred collectively as "deep diagnostic scanning devices" producing "deep images" internal to the surface of the object). Systems for use in analyzing skin and joints have used baseline images for comparing with a current scan of the skin or joint. Such comparisons usually operate by the physician observing the scans. Deep diagnostic imaging, such as of the spine of a patient using radio-frequency waves (MRI) or X-rays (CT) systems, is often useful for identifying disease or an injury, such as to the spine itself, or as a readily locatable landmark for other tissues. Present practice is to take and digitally store lots of data on a patient, including internal images, to both compare each patient's data to his/her own data, and "pools" of data from other people. Digital geometry processing techniques are often used to generate a 3D image of the inside of an object from a large series of 2D images taken around a single axis of rotation. Such series of CT images ("tomographic images" or "slices") are generally taken perpendicular to the longitudinal axis of the object such that each slice is oriented perpendicularly to the axis. Alternatively, the slices can be taken parallel with the longitudinal axis creating a series of longitudinal slices.

One problem encountered with all such scanning systems is the ability to properly analyze pictures or scans taken at different times, and using different types of scanning systems (modalities) and presents a problem which is presently beyond the reach of most automated systems. Additional, complications are presented by variations in quality between images, incomplete images, failure to adequately capture portions of the tissue due to congenital defect, and disease, injury or other conditions, such as caused by surgery. Thus, analysis of images and prescription of additional data collection and treatment currently requires an extensively trained technician. Further, it is often helpful to be able to obtain a one-to-one correspondence between the readily visible and markable skin/surface and underlying structures or pathology detectable by a variety of imaging devices (modalities). This may also facilitate clinical correlation, XRT, image guided biopsy or surgical exploration, multi-modality or interstudy image fusion, motion correction/compensation, and three-dimensional (3D) space tracking. However, current methods, (e.g. bath oil/vitamin E capsules for MRI), have several limitations including single image modality utility requiring completely different and sometimes incompatible devices for each modality, complicating the procedure and adding potential error in subsequent multimodality integration/fusion. They require a separate step to mark the skin/surface where the localizer is placed and when as commonly affixed to the skin by overlying tape, may artificially indent/compress the soft tissue beneath the marker or allow the localizer to move, further adding to potential error. Sterile technique is often difficult to achieve. Furthermore, it may be impossible to discriminate point localizers from each other or directly attain surface coordinates and measurements with cross sectional imaging techniques. In regards to the latter, indirect instrument values are subject to significant error due to potential inter-scan patient motion, nonorthogonal surface contours, and technique related aberrations which may not be appreciated as current multipurpose spatial reference phantoms are not designed for simultaneous patient imaging.

One process that can has been utilized to acquire and align surface images and compare these images is by pose estimation, particularly when the scan requires acquiring data of a 3D object. Pose estimation is a process that determines the position and orientation of known objects in 3D scenes relative to a remote observer. Humans perform pose estimation on a regular basis. Anytime somebody picks up a pencil or parallel parks an automobile they are using pose estimation to determine how to orient their hand properly to pick up the pencil or to initiate a trajectory that provides the best opportunity for parking successfully. In these two cases, the pose is determined using visual sensing, i.e. stereo vision and tactile feedback, but pose can be also derived from audio, radar, and other measurements that provide relative 3D position. Accordingly, pose estimation plays a significant role in a human's ability to interact with its environment, whether that environment is static or dynamic.

Pose estimation has been used in some computer vision applications for robotic or autonomous systems, where the system attempts to perform operations that are natural to humans. These applications include, but are not limited to, object identification, object tracking, path planning, and obstacle avoidance. Potential applications using pose estimation can be as simple as an industrial robotic system identifying a particular part from a bin of many different parts for picking up and loading into a machine, or as complex as autonomous aircraft flying in formation while navigating a terrain, or a spacecraft performing autonomous rendezvous and docking with a non-cooperative spacecraft by identifying docking features, developing an interception plan, and executing the plan. These applications however all require real-time pose estimation. Further, such systems for object pose estimation typically require that various landmarks or features (such as points, lines, corners, edges, shapes, and other geometrical shapes) must be identified and selected. A pose can then be made and registration performed using such identified references. Accordingly, such a system requires an object to have pre-identified features. Further, such methods often have difficulty with objects having same features but with different dimensions. Care must be taken in selecting such features as some objects may have the identified features but different non-identified features which could result in error.

Clearly, pose estimation can be applicable for certain robotic or autonomous systems, it also has other applications such as surface alignment. For example, surface alignment takes 3D surface measurements of multiple instances of the same object with different poses relative to the observer and applies a rigid transformation to the measurements so that each instance has the same pose relative to the observer. Surface alignment allows for automatic comparison such as defect detection in high production factory settings if one of the instances serves as a "truth" model. It also allows for the generation of complete 3D surface measurements of an object by stitching multiple 3D surface measurements from varying viewpoints. Varying viewpoints are required to generate a complete 3D surface measurement, because some regions of the surface are always occluded by others. With pose estimation, surface alignment can be performed with no knowledge of the relative pose of each surface as long as some overlap exists between the individual 3D surface measurements.

Other systems have been developed to automatically make comparisons of scanned images, the patients joint or body part being scanned are required to be immobilized using a specialized mold or jig in order to ensure proper alignment of the images for registering points on the images for making proper comparisons. Such immobilization is difficult for certain body regions and makes scanning problematic if such scans are being done at different locations. Further, the patients may require different methods for immobilization making the process more complex, time consuming, and expensive. While it may be possible to automatically make comparisons of scanned images of a patient, such systems require precise positioning of the patients joint or scanned area which again is time relatively complex, consuming and expensive. Further, such systems often require that the scanner making the scan must be consistently aligned with and/or consistently positioned relative to the surface being scanned. Other systems have been developed that require the physician to make artificial references on the surface of the patient being scanned for registering to allow for the proper alignment of the images.

Many pose estimation algorithms exist in literature, but it has now been found that the spin-image pose estimation algorithm provides the most accurate results while being robust to sensor noise and placing no surface restrictions on the object of interest other than it must be pose distinct (i.e. unlike a sphere). It also places no restrictions on the measurement technology other than it must generate a 3D surface mesh. Although the spin-image algorithm is accurate, like other robust pose estimation algorithms, the algorithm is computationally complex and the time required to compute a pose estimate is relatively long. Unfortunately, the relatively long computational time makes it inadequate for the many engineering applications that require a robust real-time pose estimation algorithm.

The fundamental principal behind a spin-image algorithm is to provide an efficient method for representing and matching individual points of an object's surface. It should be understood that by comparing and matching spin-images one is actually comparing and matching surface points. This representation is called a spin-image. By matching the spin-images of surface points in an observed scene (scanned image) to the spin-images of surface point of the "truth" model (reference image), surface point correspondences can be established. It should be understood that the truth model can be a scan, CAD model, mathematically defined surface, and the like. This matching procedure requires that each scene spin-image be compared to all reference spin-images by determining the linear correlation between the spin-images called the similarity measure. This is one of the most time-consuming portions of the algorithm and until now makes the spin-image pose estimation algorithm impractical for many applications. For an example, a typical spin-image is a 16×16 pixel image. Therefore, the spin-image is represented by an array of 256 numbers or "counts" at each of the 256 squares forming a grid over the image. To check for matches of spin-images, the 256 numbers in the spin-image for each point in the scene image must be compared to the 256 numbers in each reference spin-image. If the 3D scene image consists of a million points, and the reference spin-image also contains a million points, therefore there are a million of these 256 comparisons that must be made (256 million comparisons to check if the spin-image for one point in the scene spin-image matches the spin-image for one of the points in the reference spin-image). If multiple scene image points are to be compared to the full set of reference spin-image points, then the number of comparisons must be multiplied by the number of scene spin-image points to be matched. Therefore, spin-images with a larger number of grid squares (such as 32×32) results in even more computations to compare spin-images. Unfortunately, as a result of such a large number of comparisons that must be made, this method of using spin-image comparisons cannot be used for real-time pose estimation and is therefore not practicable for many applications.

Systems have also been developed, such as disclosed in U.S. patent application Ser. No. 13/373,456, filed on Nov. 15, 2011, and incorporated in its entirety by reference, functions by describing a 3D surface with a collection of 2D images (spin-images). The system operates such that the spin-images are represented by a substantial reduction of numbers (256 pixels are generally represented by less than 10 numbers) thus allowing for substantially quicker pose estimations. When two spin-images are compared a similarity measure (score) is generated that indicates their similarity such that the higher the score the more similar are the images. Unlike traditional methods that treat all matches equally, the subject process examines all matches based on the similarity measure and groups them using the score. The process uses the match with the highest score, creates a group and then estimates a pose. If the pose error is less than the error threshold, the process ends and the pose is estimated. If the pose error is greater than the error threshold, the process uses the match with the next highest similarity measure and repeats the process until it obtains a pose error that is less than the threshold. This process significantly increases the speed of the process such that real time comparisons can be made.

In view of the foregoing, it is apparent that a need exists for a scanning system and display for detecting and quantifying similarities or differences between collected data or images obtained from the object of interest and stored data, images, and/or virtual images, or from a previous scan and which can operate in a relative short amount of time and preferably in relative real time. Further, a need exists for a system that allows objects to be scanned without the need or with a reduced need for the object to be immobilized with a specialized mode or jig when scanned or the scanner to be in the same position relative to the object for each scan, thus placing no restrictions of how the object being scanned is positioned relative to the scanner. In addition, a need exists for a system and display that can operate to obtain a one-to-one correspondence between a readily visible skin/surface and underlying structures or pathology detectable by a variety of imaging modalities and which can operate to facilitate clinical correlation, XRT, image guided biopsy or surgical exploration, multimodality or interstudy image fusion, motion correction/compensation, and 3D space tracking.

SUMMARY OF THE INVENTION

The subject invention is a scanning system and display for detecting and quantifying similarities or differences between collected data obtained from a scanned object and stored data, or stored data used to create an image of a previous scan. In a preferred embodiment of the invention, the system comprises one or more sensing components for scanning and measuring various surface features of an object and obtain a one-to-one correspondence between readily visible skin/surface features and underlying structures or pathology detectable by a variety of imaging devices or modalities. Preferably, such surface features include the color, temperature, texture, size, shape, spatial dimensions, contour, curvature, softness, roughness, shininess/gloss, infrared signature, electrical vectors/flux, magnetic field strength/vector/flux, dynamic rebound, spatial phase characteristics, measurements derived from spatial phase characteristics, flexibility, and other such features or a combination of such features. In another preferred embodiment, the system further comprises a data analysis software module having software and/or firmware capable of comparing data retrieved from the object scanned to a database or other representation comprising data from other similar or dissimilar objects or from one or more previous scans of the object.

In a preferred embodiment of the subject invention the underlying structures of an object are detected using a deep diagnostic scanning device.

In a preferred embodiment of the invention the scanning component comprises a surface scanning device effective for capturing electromagnetic radiation.

In a preferred embodiment of the subject invention the scanning component comprises a deep diagnostic scanning device that uses X-rays, gamma rays, radio-frequency waves, electrical fields, acoustical waves, visible light, visible light reflection, infrared, microwaves, electron-position annihilation, electron, ions, or magnetic fields.

In a preferred embodiment of the subject invention the deep diagnostic imaging device is a CT or a MRI system.

In another preferred embodiment of the invention the system operates to compare two or more images taken using a deep diagnostic imaging device.

In another preferred embodiment of the invention the system operates to create a 3D surface image of an object and a deep 3D image of an object and overlaying or superimposing the 3D surface image on the deep 3D image.

In a preferred embodiment of the invention the 3D surface image is a 3D thermo image.

In a preferred embodiment of the invention the 3D surface image is a 3D color image.

In another preferred embodiment of the invention the 3D surface image is a 3D field such as created by electricity, magnetism, or electrical or electromagnetic phenomenon.

In another preferred embodiment of the invention the data analysis software module operates to detect and quantify the similarities or differences between collected data taken of the scanned object and stored (reference) data.

In another preferred embodiment of the invention the data analysis software module operates to determine differences and similarities between data obtained from two or more scans of the object in real time.

In a preferred embodiment of the invention the system software module operates system software that maps at least one image of the outer surface onto a 3D image generated using a plurality of deep images.

In a preferred embodiment of the invention the data analysis software module comprises computing hardware such as one or more apparatus consisting of central processing units (CPU's), graphics processing units (GPU's), digital signal processors (DSP's), microprocessors, field programmable gate arrays (FPGA's), very large scale integration (VLSI) systems, complex programmable logic devices (CPLD's), or systems on a chip (SOC's), and/or other such data processing devices including cell processors, biological processors, and quantum computing.

In another preferred embodiment of the invention the data analysis software module is capable of comparing the data retrieved from the scanned object to a database or other representation comprising data from other similar or dissimilar objects (reference data).

In another preferred embodiment of the invention, the data analysis software module is capable of detecting and quantifying the similarities or differences between collected data from the scanned object (scanned data) and stored data (reference data).

In a preferred embodiment of the invention, the scanning system and display operates in conjunction with robotic surgical systems.

In a preferred embodiment of the invention, the scanning system and display operates to overlay or wrap a surface image created using a surface scanning device for scanning and measuring various surface features of an object onto a 3D image created using a deep diagnostic scanning device.

Other advantages, objects, and embodiments of the invention will be apparent from the following description, the accompanying drawings and the appended claims.

BRIEF DESCRIPTION OF THE DRAWINGS

To provide a more complete understanding of the present invention and further features and advantages thereof, reference is now made to the following description taken in conjunction with the accompanying drawings, in which.

DETAILED DESCRIPTION OF THE INVENTION

Figure 1:
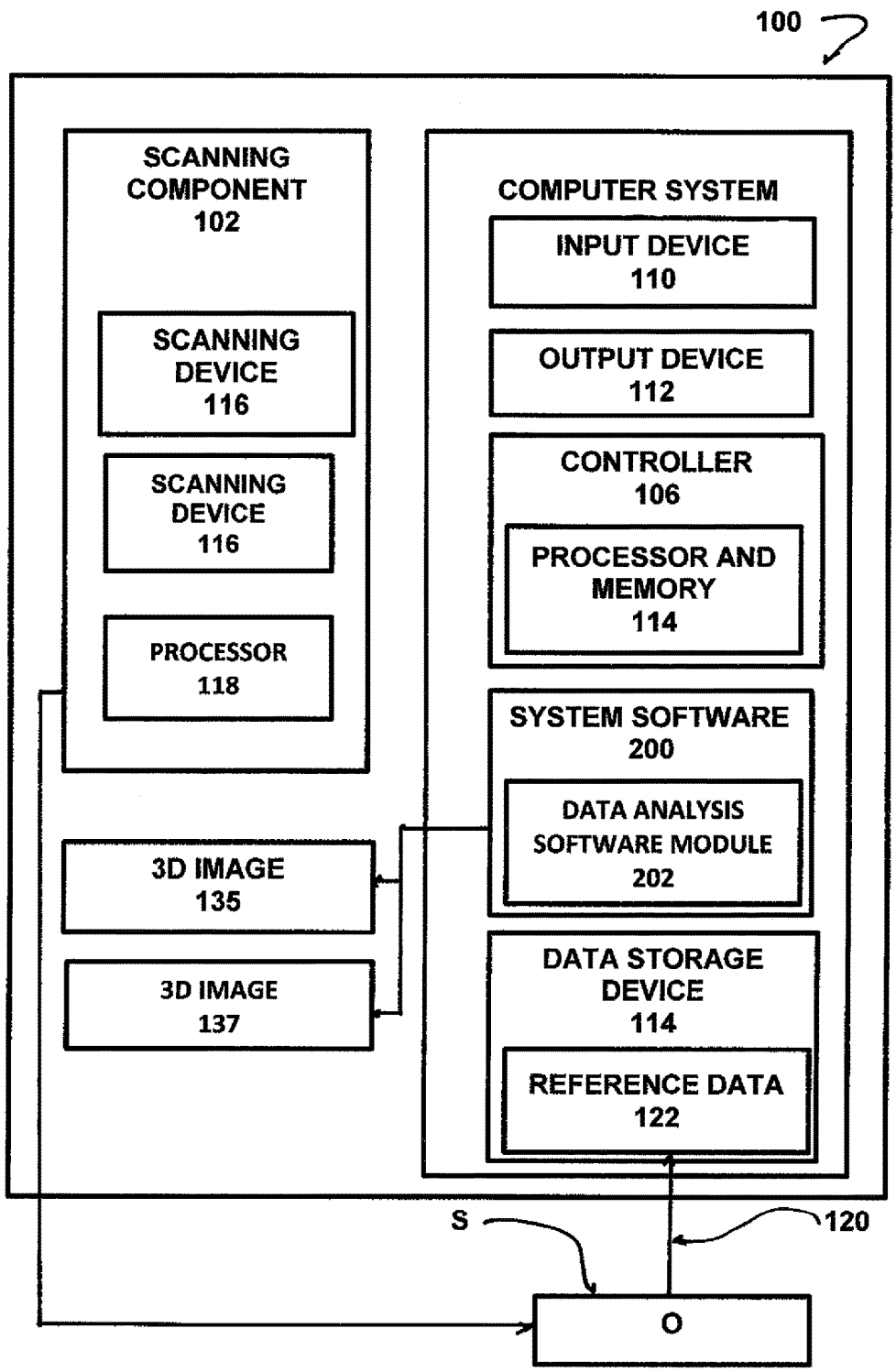
FIG. 1 is a schematic representation of a preferred embodiment of the a scanning system and display for detecting and quantifying similarities or differences between collected data obtained from the scanned object and stored data (reference data) showing a scanning component having one or more scanning devices and a computer system having at least one data storage device and system software.

Referring to FIG. 1, the scanning system and display 100 comprises a scanning component 102 and a computer system 104 for implementing and operating the system software 200 that performs the method of the subject invention. The computer system 104 includes a controller 106, a processor and a memory 108. It should be understood that the processor and memory 108 operates to perform the specific data analysis function as described herein and can comprise various computing hardware such as central processing units (CPU's), graphics processing units (GPU's), digital signal processors (DSP's), microprocessors, field programmable gate arrays (FPGA's), very large scale integration (VLSI) systems, complex programmable logic devices (CPLD's), or systems on a chip (SOC's), and/or other such data processing devices including cell processors, biological processors, and quantum computing devices. The computer system 104 further comprises other devices, such as a suitable input device, like a keypad, touch screen, or any other suitable input device 110 that can accept information; one or more suitable output devices 112, such as a computer display, printer, image-forming or display device, and the like; and a data storage device 114 such as any of the usual devices used for the storage of data, such as computer hard drives, floppy discs, binary codes, optical bits, mechanical scribes, magnetic tapes, compact discs, digital audio tapes, analog tapes, vinyl discs, and any device or devices capable of storing data. It should be understood that the computer system 104 can include any combination of the above components, or any number of different components, peripherals, and other devices. Preferably, the computer system 104 operates under the control of an operating system, such as the WINDOWS operating system developed by Microsoft Corporation or the MACINTOSH operating system developed by Apple Computer Corporation. It should be understood, however, that other operating systems could be utilized to implement the system software 200 of the scanning system and display 100 of the present invention.

Figure 2:
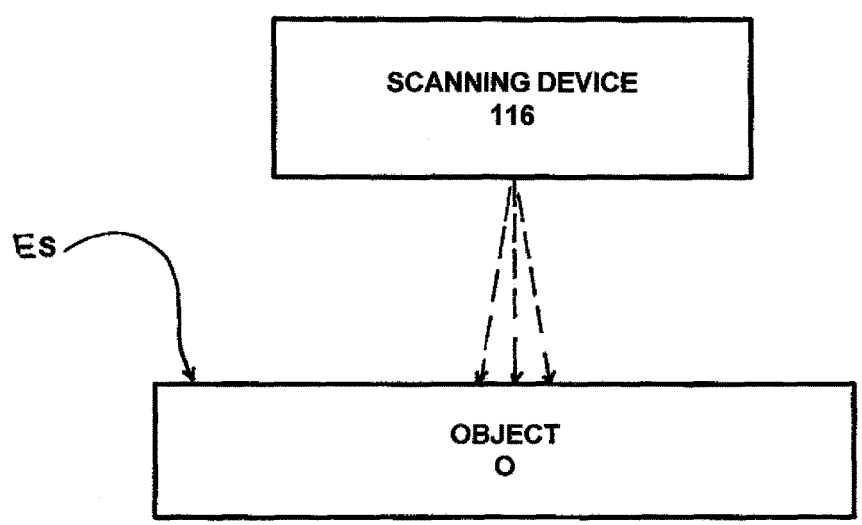
FIG. 2 is a schematic representation illustrating the general methodology of a preferred embodiment of the scanning component having a scanning device effective for obtaining a scan of an external surface of an object.

Preferably, as shown in FIG. 2, the scanning component 102 includes one or more scanning devices 116 that operate to scan and/or measure one or more various features of an object O. Such features include, but are not limited to color, temperature, texture, size, shape, spatial dimensions, contour, curvature, softness, roughness, shininess/gloss, infrared signature, electrical vectors/flux, magnetic field strength/vector/flux, dynamic rebound, flexibility, special phase characteristics, measurements derived from spatial phase characteristics, and other like features. The scanning devices 116 preferably comprise conventional scanning devices that have the capability to capture electromagnetic radiation from any part of the electromagnetic spectrum, and include, but not limited to visible light cameras, infrared cameras or detectors, ultraviolet cameras or detectors, x-ray or high-energy detectors, radio wave detectors, microwave detectors, structured light detectors, glossmeters, colorimeters, radiation dosimeters or reflectometers. The scanning devices 116 may also include microphones or other sound capturing devices, mechanical devices such as calipers or sensing wires or probes, laser distance or contour measuring devices, strain gauges or the like. It should be apparent to one skilled in the art that the scanning component 102 can comprise any surface scanning device capable for detecting and/or measuring surface or any deep diagnostic scanning device capable of obtaining data or images below the surface (internal). In another preferred embodiment of the invention the deep diagnostic scanning device 116 is capable of obtaining data by transmitting through the surface of an object. In another preferred embodiment of the invention the scanning device 116 is in the form of being both a surface scanning device and a deep diagnostic scanning device. It should now be understood the scanning component 102 can comprise one or more various scanning devices 116 such as a three-dimensional (3D) scanning device, which may include a laser; a color-detecting device (color camera); and/or a thermo imaging system (a thermo camera or laser), and other similar systems and devices. Preferably, the scanning component 102 further includes one or more processors 118 which communicate or utilize the system software 200 of the computer system 104 such as by electrical wires or other electrically conducting fibers or circuits, optical fibers, or any other wired or wireless data connection capable of transmitting data, sound waves, or images, including Internet connections, local area networks (LAN) connections, wide area networks (WAN) connections, which operate together to direct the operation of the scanning devices 116.

Referring to FIG. 1, the computer system software 200 is shown having a data analysis software (and/or firmware) module 202 which operates to compare collected data 120 retrieved from the scanned object O to reference data 122 or data from another scan stored in the data storage device 114. It should now be apparent to one skilled in the art that data analysis software module 202 can include various information mechanisms capable of performing the wide range of data analysis enabled by the usual range of available computer programs. It should be understood that the scans can be surface scans, diagnostic inner scans, or a combination thereof.

The operating components of the scanning system and display 100 and the system software 200 operates such that the scanning component 102 receives instructions inputted into the system 100 using the suitable input device 110 to cause the system software 200 to direct the operation of one or more of the scanning devices 116. Preferably, the system software 200 is also an interactive, menu and event driven system using conventional type of prompt, dialog, and entry windows to guide a user to enter information and instructions to provide an interactive communications interface between the system 100 and the users. As used herein, the term "software" refers to any form of programmed machine-readable language or instructions (e.g., object code) that, when loaded or otherwise installed, provides operating instructions to a machine capable of reading those instructions, such as a computer. The system software 200 of the present invention preferably can be stored or reside on, as well as be loaded or installed from, one or more floppy disks, CD ROM disks, hard disks or any other form of suitable non-volatile electronic storage media or can be run from a remote location such as a "cloud" or Internet site. The system software 200 can also be installed by downloading or other form of remote transmission, such as by using Local or Wide Area Network (LAN or WAN)-based, Internet-based, web-based or other remote downloading or transmission methods.

Figure 3:
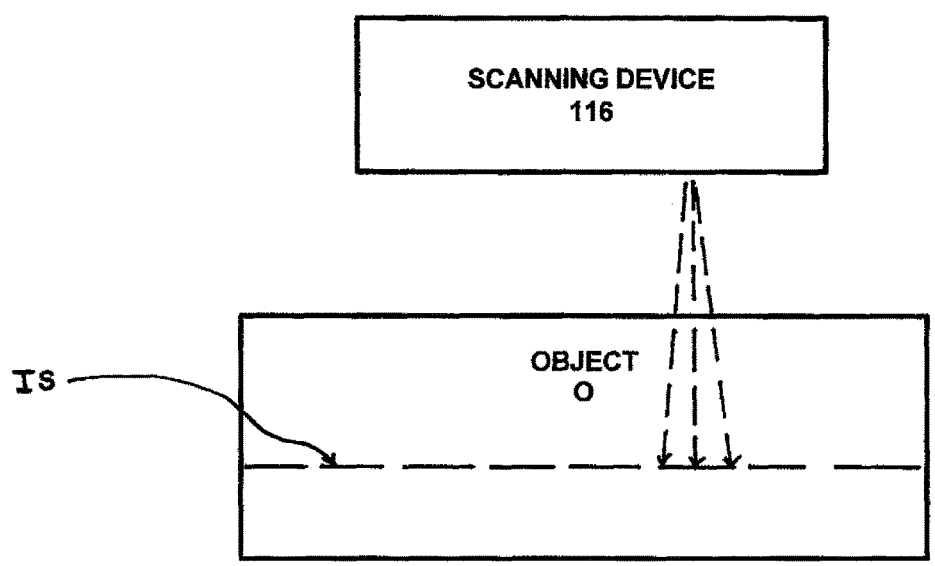
FIG. 3 is a schematic representation illustrating the general methodology showing the scanning component having a scanning device effective for obtaining a scan of a surface of an object located below the external surface of the object.
Figure 4:
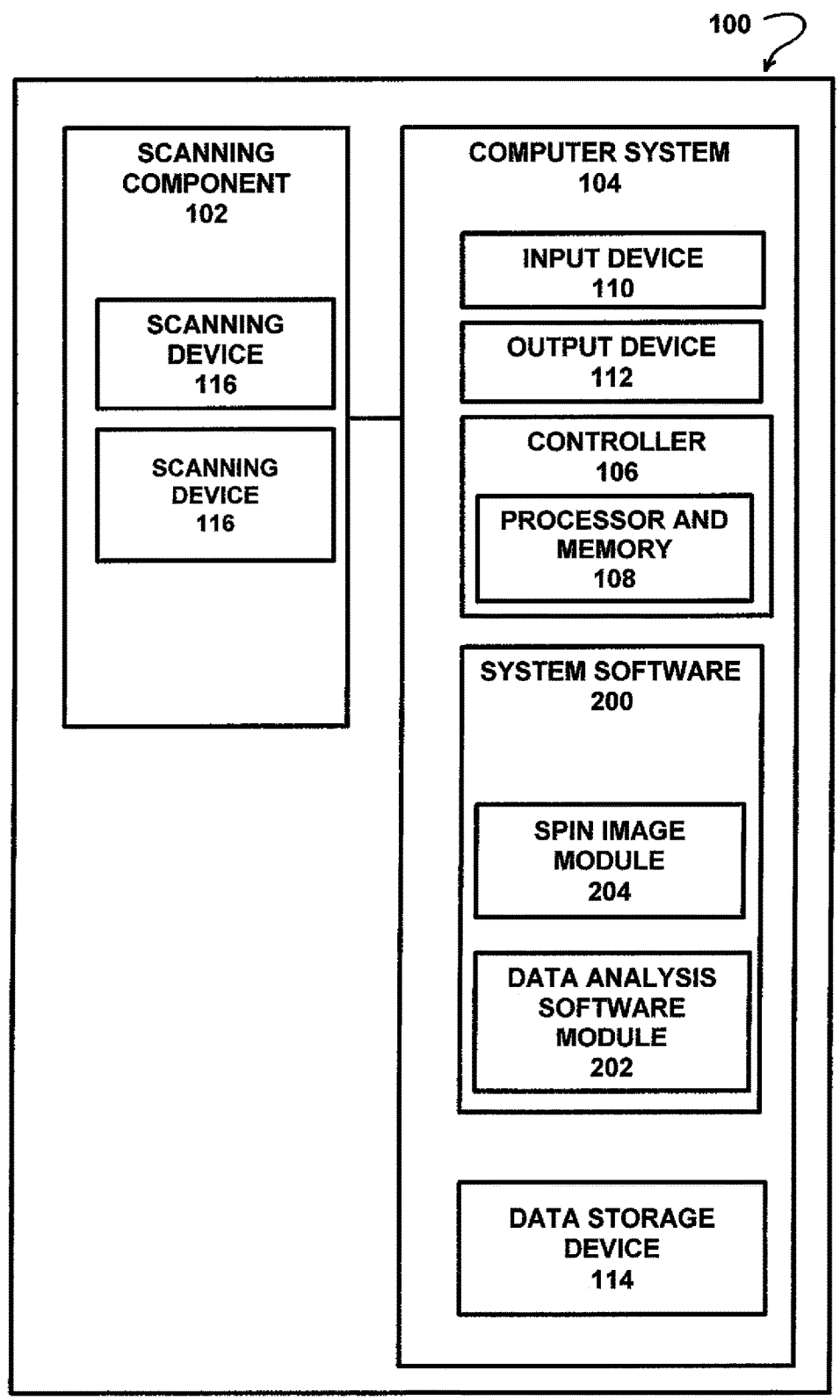
FIG. 4 is a schematic representation illustrating the general methodology of the scanning component in communication with the computer system.

An illustrative example of a preferred embodiment of the scanning system and display 100 of the subject invention is shown in FIG. 3 wherein in a preferred embodiment the scanning component 102 includes a deep diagnostic imaging scanning device 116, such as a conventional CT or MRI scanning device, that operates to take capable of detecting or measuring data transmitted through the surface of an object, such as through the skin of a person.

In another illustrative example of a preferred embodiment the scanning component 102 comprises a combination of scanning devices 116 such as a conventional CT, MRI, or ultrasound (US) scanning for taking one or more images below the surface S of an object O and a surface scanning device such as a visible light camera capable of detecting shape or form, and/or the color (such as a colorimeter) and/or the temperature (such a thermo graphical device) of the surface of the object. It should be understood that surface S can be an external or outer surface ES of an object (FIG. 2) but can also be an internal surface IS within or deep within the surface S of the object (FIG. 3). The system 100 as used herein operates to scan the outer surface S of an object O as well as scanning surfaces within the outer surface S of the object O. In one illustrative example the object is a portion of a patient, such as part of an arm, leg, knee, spine or other anatomical part of a person. These collected data 120 are then transmitted to data storage device 114 and stored as stored reference data 122 for future processing by the system software 200 and/or transmitted to the data analysis module 202 of the system software 200. Thus, the stored reference data 122 can comprise both surface reference data 123 and inner surface reference data 125.

In a preferred embodiment of the invention, the scanning device 116 uses X-rays, gamma rays, radio-frequency waves, electron-position annihilation, electron, ions and magnetic fields (hereinafter referred collectively as "deep diagnostic scanning devices" producing "internal or deep images"), such as a conventional CT, MRI, or US. The system software 200 then uses a conventional digital geometry processing technique to generate a 3D image of a layer or at a depth below the surface of an object from a large series of 2D images (such as a series of CT images, "tomographic images" or "slices") taken around a single axis of rotation.

In a preferred embodiment, the system software further operates such that at least one image using a visible light camera, is taken of the outer surface S of the object O and stored in the data storage device 114. The system software then operates to map the at least one image 135, such as an outer surface image, onto another 3D image 137, such as an inner surface image generated using the plurality of deep images within the surface of the object. One such method of mapping of comparing two images is by the process of spin-image matching.

One difficulty in comparing images or mapping one image onto another image created from two or more scans taken over a period of time using conventional computer processing is the need to ensure that common points on the two images are properly aligned. One method for properly aligning scans is by use of a process utilizing spin-images. Spin-images are generated to provide a simple representation that can be used to compare the spin-images from different points on two representations of an object to see whether they have similar spin-images. If they do, this implies the representations correspond to the same surface point. Spin-image matching is the process of determining the similarity of a scene spin-image to those in a spin-image stack (database) created from a reference model or image of that object. Due to noise, lighting, and other effects, spin-images from different instances of an object will never be exactly the same. Therefore, a meaningful way of comparing two images is required. Further, in for many applications, comparing images must be done in real-time, thus, comparing images must be done in a manner to allow for real-time comparisons. In addition, such comparisons must be made at various locations that do not permit the use of expensive, room-sized specialized computer systems.

Figure 7:
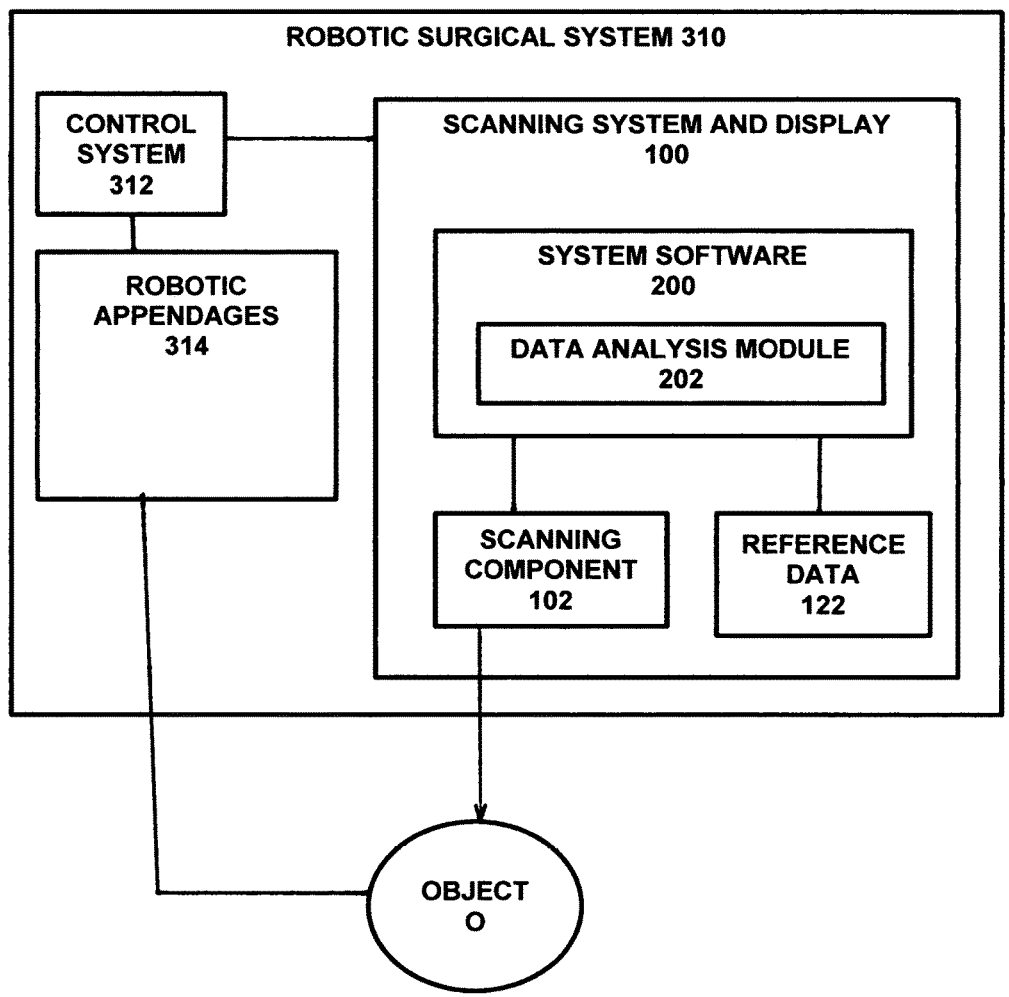
FIG. 7 is a schematic representation illustrating the general methodology of a robotic surgical system for performing a medical operation coupled to the scanning system and display of the subject application.

Referring to FIGS. 2 and 7, in a preferred embodiment of the invention, the system software 200 preferably comprises a spin-image module 204 for providing an efficient method of representing and matching individual points of an object's surface S necessary for comparing two or more scene (scanned) images. In order to parallelize the matching portion of the spin-image module 204 enough to approach real-time performance needed for many applications, while not requiring room sized, power hungry computer systems, the processor and memory 108 of the computer system 104 preferably is a graphics processing unit (GPU) for a parallel implementation of the matching portion of the spin-image module 204. In a preferred embodiment of the invention the GPU has a massively parallel, many-core computing architecture that provides teraflop computing power in a scalable, portable, power efficient, and affordable platform. One illustrative example of such a GPU is sold by Nvidia Corporation of Santa Clare, Calif.

Figure 5:
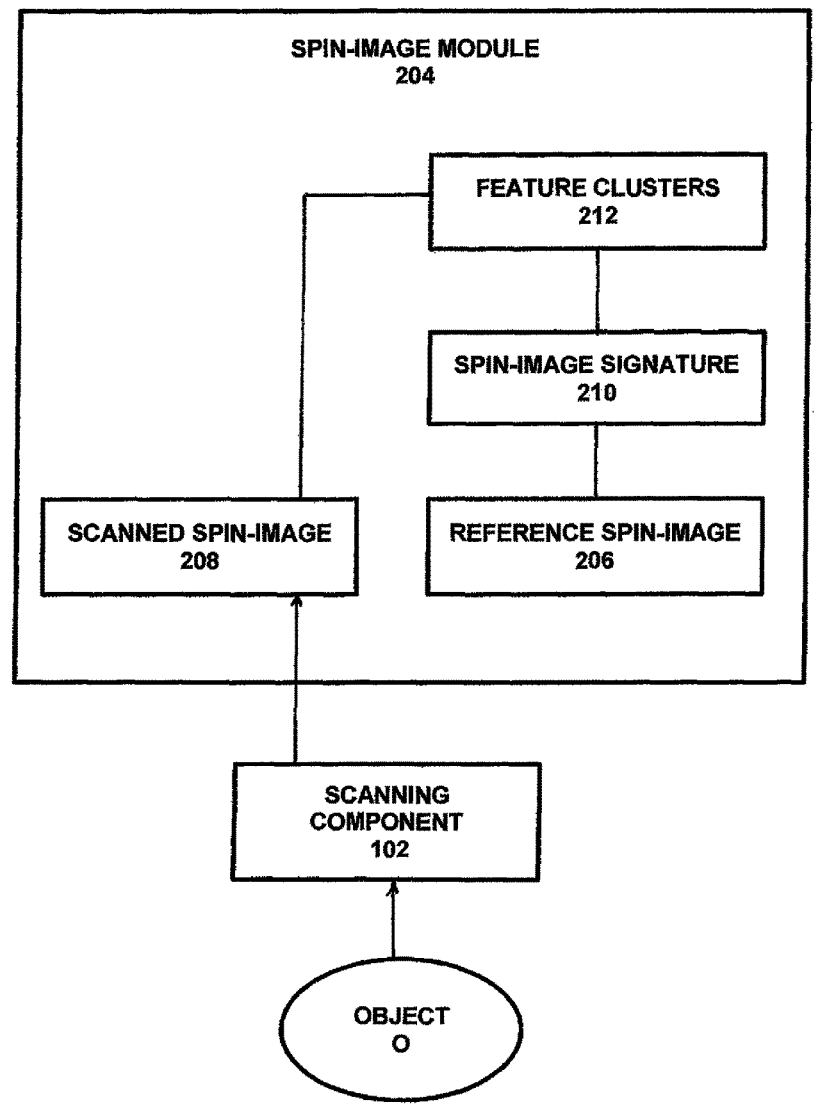
FIG. 5 is a schematic representation illustrating the general methodology of the spin-image module.

In another preferred embodiment of the invention as shown in FIG. 5, the spin-image module 204 operates such that the matching operation restricts reference spin-images 206 (obtained from previous scans of an object) by comparing only those most likely to match the scene spin-image 208 (obtained from a scan of an object that is being compared to reference spin-images). The spin-image module 204 operates by using a spin-image signature 210 (reduced-order representation of a spin-image) to identify feature clusters 212 in the set of reference spin-images 206. The spin-image module 204 further operates to find the degrees of membership of a scene (scanned) spin-image 208 to the clusters 212 of the set of reference spin-images 206. The reference spin-images 206 are then filtered by comparing the reference spin-images 206 and determining the degrees of membership similar to that of the scene (scanned) spin-image of interest 208. A similarity measure is than determined and grouped in accordance with the similarity measure and checked to ensure that the two images are geometrically consistent and then a pose is estimated. One such method of comparing and/or superimposing and/or overlaying images is shown and described in U.S. patent application Ser. No. 13/373,456, filed on Nov. 15, 2011, and incorporated in its entirety by reference.

It should now be apparent to one skilled in the art that the above-described system and process provide an efficient method of representing and matching individual points of an object's surface S necessary for aligning two or more scanned images. Once the images are properly aligned (superimposed one over another) using a global alignment method such as by the process described above, the system operates to compare the images. Once the "same" surface points are located, differences in any available surface data can be computed. For example: surface displacement, color differences, thermal differences, etc. (It should be understood that all measured surface data can be compared.

In another illustrated example of the process described above, is shown in FIG. 6, whereby a manufacturing apparatus 300, such as a robotic apparatus, for automatically performing a mechanical operation is in communication with or comprises the scanning system and display 100 of the subject application. In an illustrative example, an object O, such as an individual part (for example a screw, sprocket or other object) is to be installed in the manufacturing apparatus 300. A robotic arm 302 is shown having a clasping mechanism 304 effective for clasping the object O and placing it properly into the assembly 308. The scanning component 102 of the scanning system and display 100 operates to scan the object O and the data analysis module 202 of the system software 200 functions as described above to compare the collected scanned data 120 (scene image) with stored reference data 122 (reference image) to determine the alignment of the object O. The system software 200 then operates to communicate with the control system 306 of the robotic apparatus 300 providing instructional information to adjust the object into proper alignment such as for placement of the object into an assembly 308. The control system 306 and the data analysis module 202 function together such that that the robotic arm 302 and the clasping mechanism 304 properly performs the desired operation. It should be apparent that the scanning system and display 100 allows objects, such as parts, to be identified and the orientation of the object (as described below) to be analyzed so that the robotic operation can automatically be adjusted if necessary without the need to pause operations of the assembly.

Figure 6:
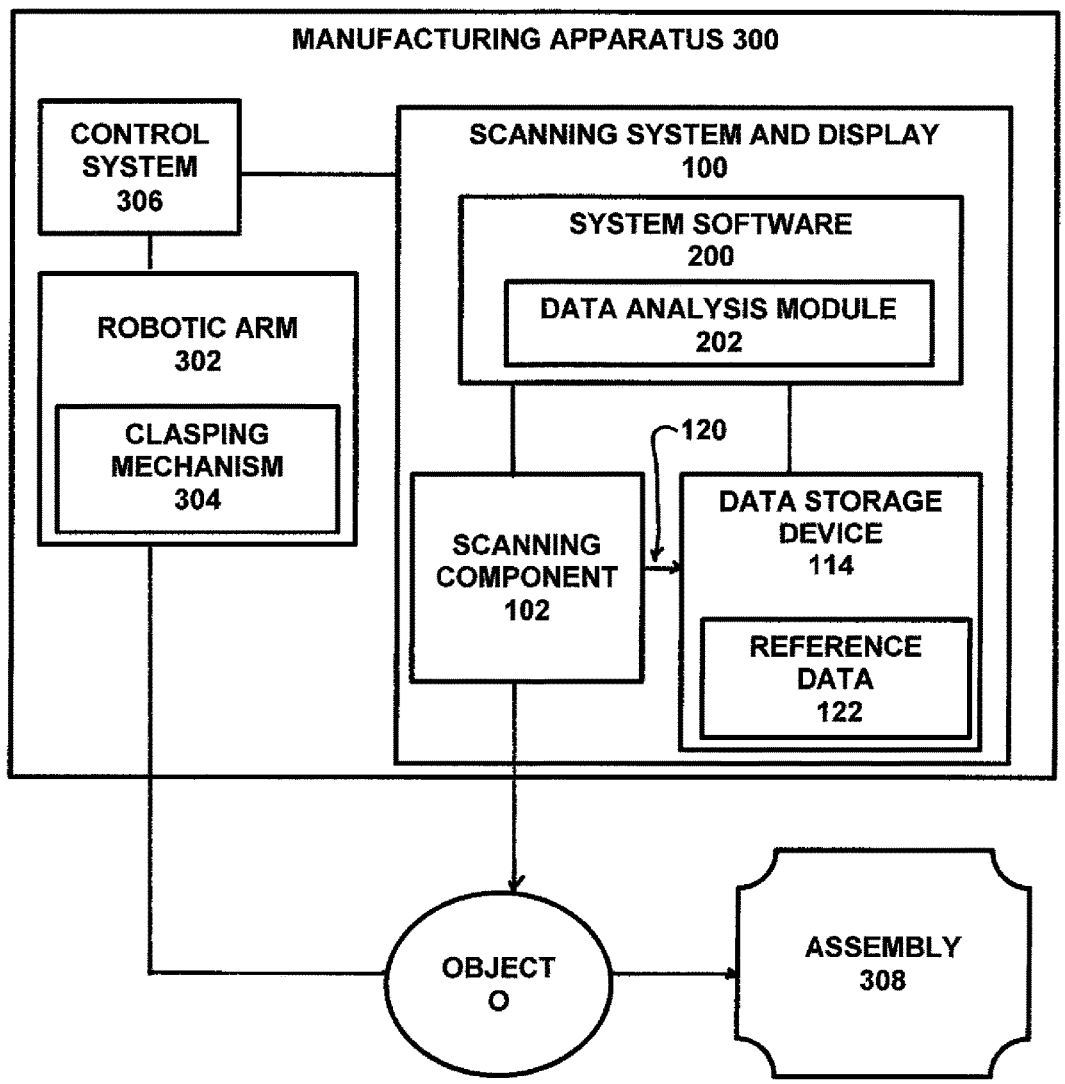
FIG. 6 is a schematic representation illustrating the general methodology of a manufacturing apparatus for performing a desired operation coupled to the scanning system and display of the subject application.

In another illustrative example is shown in FIG. 6, a robotic surgical system 310 comprises or is in communication with the scanning system and display 100 of the subject invention and includes a control system 312 for controlling one or more robotic appendages 314 that operate to perform a medical treatment operation such as surgery. The data analysis module 202 cooperates with the control system 312 of the robotic surgical system 310. The data analysis component 202 operates as described to compare reference stored image or data 122 of an object O, such as a part of a patient, with subsequent scene (scanned) images or data 120 and using the comparisons operates to calculate adjustments which are communicated to the control system 312 which directs the necessary adjustments to one or more of the robotic appendages 314. In another illustrative example, the system 100 operates such that the display device provides a notification for alerting a surgeon when the surgeon is in close proximity to biological landmarks or critical body parts, like the facial nerve for example. The data analysis component 202 operates as described to compare reference stored image or data 122 of and object O, such as a part of a patient, with subsequent scene (scanned) images or data 120. The reference stored image or data can be derived from CT, MRI, or other penetrative scanning technologies. Aligning surface scans performed during surgery then provides a reference to internal measurement available in the reference stored image. This enables the system to notify the surgeon whether they are in proximity to internal or external body parts of interest.

In another illustrative example, the scanning system and display can be used by a physician or a trainer to reduce repetitive motion injuries and athletic injuries and/or gauge a person's response to treatment or to therapy. In one preferred method, a person is asked where he/she is having symptoms, such as pain, stiffness, tightness, warmth, tingling, or other sensations on a limb or other body part. Alternatively, the person may indicate the location of such symptoms in writing or marking the location of the problem on a diagram, photograph, physical model, computer or electronic image, or outline of the body part. Likewise, a physician or trainer can write such symptoms down or could indicate these problems, or objective signs the physician or trainer observes, on a diagram, drawing, outline, computer or electronic image, physical model, or photograph of the body part. In another preferred embodiment, the person and/or physician or trainer can mark the location of the symptoms/signs on the actual surface of the person's body part with markings, either drawn onto the body surface or by attaching some 3D marker. Then, surface and/or deep scans of the relevant body part could be obtained using the scanning system and display of the subject invention. The system can then operate can align such surface markers or data with deep data obtained by the system, thus aiding the physician or trainer in watching for the development of abnormal changes, both surface and deep, that can indicate incipient problems or tissue injury. For example, a baseball pitcher's elbow or shoulder could be scanned, either with deep and/or surface scans, between innings or after every so many throws to watch for increases in swelling, temperature, redness, or other signs of impending tissue damage.

Figure 8:
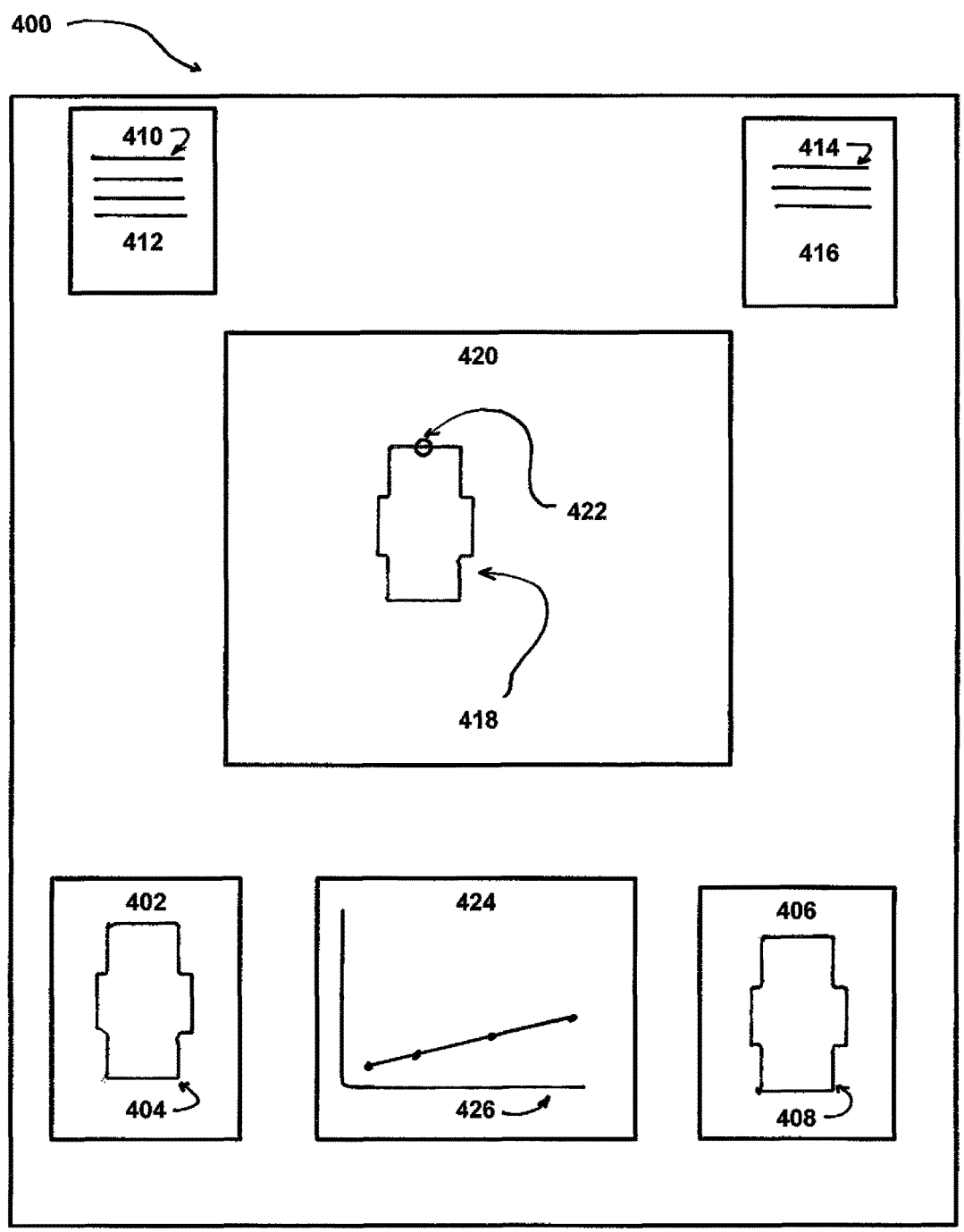
FIG. 8 is a schematic representation of a display presented on an output device showing two separate scanned images and a composite image for use in analyzing differences between the two separate scanned images.

Referring to FIGS. 1 and 8, a schematic representation of a display 400 is presented on an output device 112 of the computer system 104. The display 400 includes a first window 402 showing a first scanned image 404 created from stored reference data 122 and a second window 406 showing a second scanned image 408 created from stored reference data 122. Preferably the scanned images 404 and 406 have each been taken using a scanning system and display 100 as described above. It should be understood, however, other conventional scanning systems capable of creating 3D images may also be used and store data as stored reference data 122. A listing of scanned images 410 stored as stored reference data 122 is displayed in a first listing window 412. When a user selects specific scanned image from the list of scanned images 410, the scanned image 404 is displayed in the first window 402. The system software 200 then operates to create listing of all subsequent scans 414 and displays the list in a second listing window 416. The user then can select a second or subsequent scanned image created from stored reference data 122 which is displayed in the second window 406. The system software 200 then operates, as described above, and maps (superimposes) the two images together to create a composite scan image 418 which is displayed in a comparison window 420 which can then be used by the user in analyzing differences between the two separate scanned images 404, 408. It should be understood that the first scanned image 404 and the second scanned image 408 can represent different types of data. For example, the images could represent various features of an object including color, temperature, texture, size, shape, spatial dimensions, contour, curvature, softness, roughness, shininess/gloss, infrared signature, electrical vectors/flux, magnetic field strength/vector/flux, dynamic rebound, flexibility, special phase characteristics, measurements, and other like features. In a preferred embodiment the user can select a specific point 422 on the composite scan image 418 using the input device 110 and the measured difference between the stored reference data 122 creating the first scanned image 404 at the selected specific point 422 and the stored reference data 122 creating the second scanned image 408 at the selected specific point 422 is calculated and the result is displayed in a selected point history window 424. In another preferred embodiment the history window 424 is provided showing the history 426 (relative measured changes) at the selected specific point 422 for all of the stored reference data 122 is displayed. It should be apparent that a user can then use can create images and calculate changes between the images and/or specific points on the images for different scanned parameters to make analytic determinations. For example, various scans of a medical patient showing a specific rash or wound can be displayed and a user can then determine, looking at differences in the images or as shown on a comparison image for a scanned parameter (such as, but not limited to size (swelling) changes, area changes, color changes, temperature changes), if the rash or wound is improving over time. Specific points of interest along the rash or wound can be selected and using the display of the history window 424 the user can determine the history of the rash or wound by looking at the changes over time of a scanned parameter. By comparing the history 426 of the rash or wound with medical treatment, the user can determine if various treatments are or are not effective.

It should now be apparent that the scanning system and display of the subject invention operates and is effective to detect and quantify similarities or differences between collected data (or a set of stored reference data) obtained from an object of interest and other collected data (or another set of stored reference data) and which can operate in a relative short amount of time and preferably in relative real time. The system operates utilizing a method or process that decreases the time required for calculating a pose estimate such as by the use of a spin-image algorithm, thus increasing its performance thereby making it more practical for many applications that require real-time operations. In a preferred embodiment of the invention the system comprises one or more sensing components each having a scanning device. Preferably, the scanning devices operate to perform a surface scan of the object and/or performing a deep scan within the surface of the object. In a preferred embodiment, the scanning devices operate to measure and/or obtain data of various surface features of an object, including one or more of the following: color, temperature, texture, size, shape, spatial dimensions, contour, curvature, softness, roughness, shininess/gloss, infrared signature, electrical vectors/flux, magnetic field strength/vector/flux, dynamic rebound, flexibility, spatial phase characteristics, measurements derived from spatial phase characteristics, and other such features. Preferably the system comprises a data analysis component having software and/or firmware capable of comparing data retrieved from the object scanned to a reference database or other representation comprising data from other similar or dissimilar objects or from one or more previous scans of the object. In a preferred embodiment, the scanning system and display of the subject invention further operates to determine differences between data obtained from two or more scans of the object.

In another preferred embodiment of the invention the scanning system and display comprises software and/or firmware capable of comparing the data retrieved from the scanned object to a database or other representation comprising data from other similar or dissimilar objects and is capable of detecting and quantifying the similarities or differences between collected data from the scanned object and stored data. The system software performs the method of representing the local topography of the object as a 2D histogram that is invariant to rigid transformations and creates model spin-images for the generation of plausible scanned-model point correspondence for use to generate pose estimates. Thus, it should now be apparent that two or more scans, such as scans showing dimensions, color, temperature, and the like, can be placed in overlapping position using pose estimation allowing an image that shows changes to such parameters. This can be done in real time (less than about 1 minute). It should also now be apparent to one skilled in the art that the subject invention can operate to scan numerous objects including, but not limited to mechanical objects, biological objects or medical conditions, artifacts, geographical objects, agricultural objects, or used in conjunction with robotic manufacturing systems, robotic surgical systems, aircraft systems, and marine applications.

It should be apparent to one skilled in the art that the scanning system and display of the subject invention that surface scan data or images can be compared to deep scan data or images of the same structural or anatomical region taken at the same time or at different times. In a preferred embodiment of the invention, one surface scan can be overlaid or mapped onto a deep scan. Accordingly, It should also now be apparent to one skilled in the art that data or scans obtained from various scanning devices (e.g. CT) can be compared to data or images taken using other scanning devices (e.g. MRI, X-ray, tomography, positron emission tomography, mammography, ultrasound, electric field vectors or imaging or other such surface scanning systems). It should also now be apparent to one skilled in the art that the present invention operates to allow comparisons between actual or real images or data and virtual images or data; thus, real images or data can be compared to other real images or data, virtual images or data can be compared to other virtual images or data, and real images or data can be compared to virtual images or data. Further, two or more images or data, whether obtained at the same time using the same scanning device, or over sequential time Periods. It should also now be apparent to one skilled in the art that the scanning system and display of the subject invention operates to permit various data and images from one or more deep scans and one or more surface scans to be matched and aligned, such that certain swelling or tissue layer to be placed in the proper, actual position in space relative to any feature of the object's surface, such as surface colors, contours, and/or other data, including but not limited to thermal, electrical, acoustical, magnetic, or chemical/compositional data. Similarly, one skilled in the art can also now see that deep scan data or images can be aligned to other deep scan data or images whereby contour outlines of the deep layers are reassembled from separate slice images to create a 3D deep layer image and compared to other, subsequent deep layer images of the same object.

It should now be apparent to one skilled in the art that the scanning system and display of the subject invention that the deep or inner scan data or images can now be aligned to other deep scan data or images and that the contour outlines of the deep layers, rather than the structure's surface layers can be reassembled from the separate slice images to create a 3D deep layer image and then one deep layer image can be compared to other subsequent deep layer images of the same object as taught in the subject invention.

It should also now be apparent to one skilled in the art that the scanning system and display of the subject invention can operate to align line segments, such as diameters, radii, and chords within the image slices. For an example, similar line segments can be obtained from simultaneous or subsequent surface or deep scan data or images, and these line segments are compared and aligned to match the various scans to create a best fit or overlay. It should also now be apparent that many features of the slice or scan images, such as a circumscribed area or volume, can be used to align any number of deep or surface scans, obtained by any scanning modality. It should be understood the system can operate to scan numerous objects including mechanical objects, biological objects or medical conditions, artifacts, geographical objects, agricultural objects, or used in conjunction with robotic manufacturing systems, robotic surgical systems, aircraft systems, and marine applications.

The scanning system and display of the subject invention provides a structured methodology and design utilized by the system software and is not limited solely to the specific design of the software. Although the foregoing invention has been described in some detail for purposes of clarity of understandings, it will be apparent that certain changes and modifications may be practiced within the scope of the appended claims. It should now be apparent that the various embodiments presented can be easily modified while keeping within the scope and spirit of the subject invention. Accordingly, it should be understood that the present disclosure is to be considered as exemplary of the principals of the invention and is not intended to limit the invention to the embodiments and the specific examples illustrated and the invention is not to be limited to the details given herein, but may be modified within the scope and equivalents of the descriptions and examples contained herein.

In view of the foregoing, it should be apparent that the scanning system and display of the subject invention is effective for detecting and quantifying similarities or differences between collected data or images obtained from the object of interest and stored data, images, and/or virtual images, or from a previous scan and which can operate in a relative short amount of time and preferably in relative real time. Further, the system that allows objects to be scanned without the need or with a reduced need for the object to be immobilized with a specialized mode or jig when scanned or the scanner to be in the same position relative to the object for each scan, thus placing no restrictions of how the object being scanned is positioned relative to the scanner. In addition, the scanning system and display can operate to obtain a one-to-one correspondence between a readily visible skin/surface and underlying structures or pathology detectable by a variety of imaging modalities and which can operate to facilitate clinical correlation, XRT, image guided biopsy or surgical exploration, multimodality or interstudy image fusion, motion correction/compensation, and 3D space tracking.

We claim:

1. A scanning system and display for scanning an object comprising:
   one or more surface scanning devices that operate to a create a first collected data set of the surface of the object; and
   one or more deep diagnostic imaging scanning devices that operate to scan and create a second collected data set of an inner image below the surface of the object;
   wherein the scanning system and display operates to align said first collected data set with said second collected data set;
   wherein the scanning system and display operates to create a three dimensional inner surface image using said second collected data set and a three dimensional outer surface image using said first collected data set; and
   wherein said inner surface image is aligned with said outer surface image.

2. The scanning system and display of claim 1 wherein said one or more surface scanning devices are effective for capturing electromagnetic radiation.

3. The scanning system and display of claim 1 wherein said one or more deep scanning devices includes a deep diagnostic scanning device that uses one or more of the following: X-rays, gamma rays, radio-frequency waves, electrical fields, acoustical waves, visible light, visible light reflection, infrared, microwaves, daelectron-position annihilation, electron, ion, and magnetic fields.

4. The scanning system and display of claim 1 wherein said one or more deep scanning devices comprise a CT or a MRI system.

5. The scanning system and display of claim 1 is in communication with a manufacturing apparatus.

6. The scanning system and display of claim 1 is in communication with a robotic apparatus.

7. A scanning system and display for detecting and quantifying similarities or differences between collected data obtained from a scanned object and stored data comprising:
   a data storage device for storing one or more sets of stored reference data, wherein said one or more sets of stored reference data comprises first inner surface reference data;
   one or more scanning devices for scanning various surface features of an object to obtain one or more sets of collected data and storing said one or more sets of collected data its said data storage device;
   wherein the scanning system and display operates to align said one or more sets of collected data with said one or more sets of stored reference data;
   wherein said scanning system and display then operates to create a three dimensional first inner surface image using said aligned one or more sets of stored reference data and a second inner surface image using said aligned one or more sets of collected data;
   wherein said scanning system and display then operates to detect and quantify similarities or differences between said first inner surface image and said second inner surface image.

8. The scanning system and display of claim 7 wherein said one or more scanning devices comprises a surface scanning device effective for capturing electromagnetic radiation.

9. The scanning system and display of claim 7 wherein said one or more scanning devices comprises a deep diagnostic scanning device that uses one or more of the following: X-rays, gamma rays, radio-frequency waves, electrical fields, acoustical waves, visible light, visible light reflection, infrared, microwaves, daelectron-position annihilation, electron, ion, and magnetic fields.

10. The scanning system and display of claim 7 wherein said one or more scanning devices comprises a CT or a MRI system.

11. A scanning system and display for scanning the surface of an object and below the surface of the object comprising:
   a data storage device;
   one or more surface scanning devices that operate to scan and take surface data of the object and store said surface data in said data storage device; and
   one or more deep scanning devices that operate to scan and take internal data below the surface of the object and store said internal data in said data storage device;
   wherein said scanning system and display operates to align said surface data with said internal data.

12. The scanning system and display of claim 11 wherein said scanning system and display operate to create a three dimensional image comprising an inner surface image created using said aligned internal data and an outer surface image is created using said aligned surface data.

13. The scanning system and display of claim 11 wherein said one or more scanning devices comprises a surface scanning device effective for capturing electromagnetic radiation.

14. The scanning system and display of claim 11 wherein said one or more scanning devices comprises a deep diagnostic scanning device that uses one or more of the following: X-rays, gamma rays, radio-frequency waves, electrical fields, acoustical waves, visible light, visible light reflection, infrared, microwaves, daelectron-position annihilation, electron, ion, and magnetic fields.

15. The scanning system and display of claim 11 wherein said one or more scanning devices comprises a CT or a MRI system.

16. The scanning system and display of claim 11 wherein the alignment of said surface data with said internal data is performed by computing a pose estimate of said surface data relative to said internal data.

* * * * *